United States Patent
Kawaguchi et al.

(10) Patent No.: US 10,617,437 B2
(45) Date of Patent: Apr. 14, 2020

(54) MEDICAL TREATMENT IMPLEMENT

(71) Applicant: OLYMPUS CORPORATION, Tokyo (JP)

(72) Inventors: Yuki Kawaguchi, Koshu (JP); Ojiro Kitamura, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 629 days.

(21) Appl. No.: 15/259,480

(22) Filed: Sep. 8, 2016

(65) Prior Publication Data

US 2017/0071617 A1    Mar. 16, 2017

Related U.S. Application Data

(63) Continuation of application No. PCT/JP2016/065296, filed on May 24, 2016.

(30) Foreign Application Priority Data

Sep. 11, 2015 (JP) .................... 2015-179147

(51) Int. Cl.
A61B 17/28 (2006.01)
A61B 18/08 (2006.01)
(Continued)

(52) U.S. Cl.
CPC .... A61B 17/2812 (2013.01); A61B 17/00234 (2013.01); A61B 17/29 (2013.01);
(Continued)

(58) Field of Classification Search
CPC .... A61B 17/2909–2017/2925; A61B 17/2812; A61B 17/00234; A61B 17/29;
(Continued)

(56) References Cited

U.S. PATENT DOCUMENTS 5,312,023 A * 5/1994 Green ............... A61B 17/07207
227/175.1
5,478,003 A * 12/1995 Green ............... A61B 17/07207
227/176.1
(Continued)

FOREIGN PATENT DOCUMENTS

JP    2004-154164 A    6/2004
JP    2006-102093 A    4/2006
(Continued)

OTHER PUBLICATIONS

International Search Report dated Aug. 30, 2016 issued in International Application No. PCT/JP2016/065296.
(Continued)

Primary Examiner — Tan-Uyen T Ho
Assistant Examiner — Charles M Wei
(74) Attorney, Agent, or Firm — Scully, Scott, Murphy & Presser, P.C.

(57) ABSTRACT

A medical treatment implement including: a shaft extending along a longitudinal axis; a housing having distal and proximal portions, a proximal end of the shaft being attached to the distal portion of the housing to extend from the distal to the proximal portion, the elongated shaft being rotatable about the longitudinal axis relative to the housing; an effector attached to a distal end of the shaft, the effector articulating relative to the longitudinal axis; a drive mechanism having an output connected to the effector to articulate the effector relative to the shaft; and an input unit attached to the housing at a position closer to the proximal portion than the distal portion, wherein the input unit receives an operation input and directly inputs the drive mechanism in response to the input, wherein the input unit rotates about the longitudinal axis together with the shaft relative to the housing.

15 Claims, 8 Drawing Sheets

(51) Int. Cl.
*A61B 18/14* (2006.01)
*A61B 17/00* (2006.01)
*A61B 17/29* (2006.01)

(52) U.S. Cl.
CPC ........ *A61B 18/085* (2013.01); *A61B 18/1442* (2013.01); *A61B 2017/00424* (2013.01); *A61B 2017/2926* (2013.01); *A61B 2017/2927* (2013.01); *A61B 2017/2929* (2013.01)

(58) Field of Classification Search
CPC .. A61B 17/068–076; A61B 17/28–295; A61B 2017/305; A61B 2017/2927–293; A61B 2017/00389; A61B 2017/00393; A61B 2017/2926; A61B 18/085; A61B 18/1442
See application file for complete search history.

(56) References Cited

U.S. PATENT DOCUMENTS

| | | | | |
|---|---|---|---|---|
| 5,643,294 | A * | 7/1997 | Tovey | A61B 17/29 606/148 |
| 5,901,895 | A * | 5/1999 | Heaton | A61B 17/07207 227/176.1 |
| 2006/0190034 | A1 * | 8/2006 | Nishizawa | A61B 17/29 606/205 |
| 2009/0272784 | A1 * | 11/2009 | Farascioni | A61B 17/07207 227/176.1 |
| 2012/0074200 | A1 | 3/2012 | Schmid et al. | |
| 2012/0078244 | A1 * | 3/2012 | Worrell | A61B 17/07207 606/33 |
| 2012/0109154 | A1 * | 5/2012 | Ross | A61B 17/072 606/139 |
| 2012/0130420 | A1 * | 5/2012 | Nicholas | A61B 17/07207 606/205 |
| 2015/0066022 | A1 * | 3/2015 | Shelton, IV | A61B 18/082 606/41 |
| 2015/0090766 | A1 | 4/2015 | Milliman et al. | |

FOREIGN PATENT DOCUMENTS

| | | |
|---|---|---|
| JP | 2007-151595 A | 6/2007 |
| JP | 2010-500149 A | 1/2010 |
| JP | 2010-075375 A | 4/2010 |
| JP | 2010-088639 A | 4/2010 |
| JP | 2012-110675 A | 6/2012 |
| JP | 2013-540002 A | 10/2013 |

OTHER PUBLICATIONS

English abstract only of WO 2008/020964 A2.
English translation of International Preliminary Report on Patentability dated Mar. 22, 2018 together with the Written Opinion received in related International Application No. PCT/JP2016/065296.
Japanese Office Action dated Aug. 22, 2017 in Japanese Patent Application No. 2017-522437.
Japanese Office Action dated Jun. 6, 2017 in Japanese Patent Application No. 2017-522437.

* cited by examiner

MEDICAL TREATMENT IMPLEMENT

CROSS-REFERENCE TO RELATED APPLICATION

The present application is a continuation of PCT/JP2016/065296 filed on May 24, 2016, which is based upon and claims the benefit to JP 2015-179147 filed on Sep. 11, 2015, the entire contents of each of which are incorporated herein by reference.

BACKGROUND

Field

The present application relates to a medical treatment implement in which an end effector for treating a treatment target articulates with respect to an elongated shaft.

Prior Art

The specification of U.S. Unexamined Patent Application Publication No. 2015/0066022 and the specification of U.S. Unexamined Patent Application Publication No. 2015/0090766 each describe a medical treatment implement in which a sheath is installed to a holdable housing such that the sheath is rotatable about a longitudinal axis. In each of these medical treatment implements, the sheath and an end effector rotate about the longitudinal axis with respect to the housing in response to an operation input supplied through a rotation control knob (rotation control input unit) provided on the sheath. Further, in each of the treatment implements, the end effector can be articulated with respect to the sheath, and the angle of the end effector with respect to the sheath (the longitudinal axis) changes when the end effector articulates. As the articulation control input unit through which the operation input for articulating the end effector is supplied, an articulation control dial is attached to the housing according to the specification of the foregoing U.S. Unexamined Patent Application Publication No. 2015/0066022, and an articulation control knob is attached to the outer peripheral surface of a rotation control knob (sheath) according to the specification of the foregoing U.S. Unexamined Patent Application Publication No. 2015/0090766.

According to the specification of U.S. Unexamined Patent Application Publication No. 2015/0066022, the articulation control dial rotates independently of the rotation control knob (sheath), so that when the rotation control knob is rotated about the longitudinal axis, the articulation control dial does not rotate together with the sheath and the end effector. Hence, the relative relationship between the articulation direction of the end effector and the operational direction (the rotational direction) set by the articulation control dial changes as the angular position of the end effector about the longitudinal axis is changed in response to an operation input supplied through the rotation control knob. This makes it difficult for an operator to know the articulation direction of the end effector, leading to deteriorated ease of operation for articulating the end effector.

According to the specification of U.S. Unexamined Patent Application Publication No. 2015/0090766, the articulation control knob is attached to the outer peripheral surface of the rotation control knob connected to the distal side of the housing and rotates about the longitudinal axis together with the rotation control knob. This makes it difficult to give an operation input through the articulation control knob by using only the hand holding the housing (i.e. one hand), depending on the angular position of the articulation control knob about the longitudinal axis. Thus, ease of operation for articulating the end effector is deteriorated.

SUMMARY

The present embodiments have been made with a view toward solving the above problem, and an object is to provide a medical treatment implement that ensures ease of operation for articulating an end effector with respect to a sheath regardless of the angular position of the end effector about a longitudinal axis.

Accordingly, a medical treatment implement comprising: an elongated shaft configured to extend along a longitudinal axis; a housing comprising a distal portion and a proximal portion, a proximal end of the elongated shaft being attached to the distal portion of the housing such that the longitudinal axis extends from the distal portion to the proximal portion, wherein the elongated shaft is configured to be rotatable about the longitudinal axis with respect to the housing; an end effector attached to a distal end of the elongated shaft, wherein the end effector is configured to articulate with respect to the longitudinal axis of the elongated shaft; a drive mechanism having an output connected to the end effector, the drive mechanism configured to articulate the end effector with respect to the elongated shaft; and an articulation control input unit attached to the housing at a position closer to the proximal portion than the distal portion, wherein the articulation control input unit is configured to receive an operation input and directly input the drive mechanism in response to the operation input, wherein the articulation control input unit is configured to rotate about the longitudinal axis together with the elongated shaft with respect to the housing.

DESCRIPTION OF PREFERRED EMBODIMENTS

First Embodiment

A first embodiment will be described with reference to FIG. 1 to FIG. 5.

Figure 1:
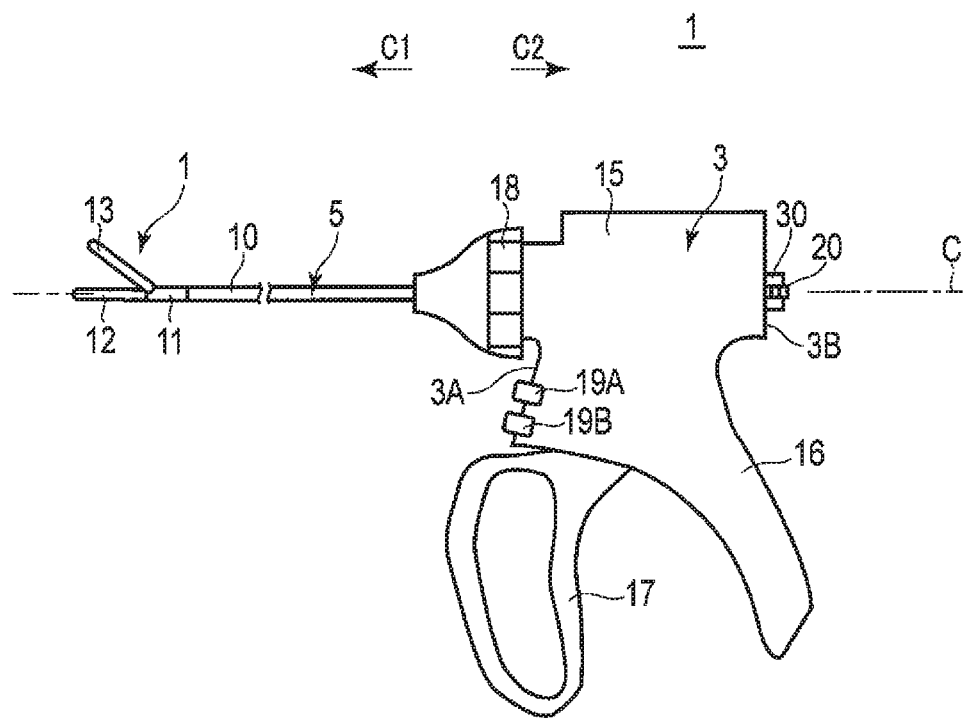
FIG. 1 illustrates a schematic diagram of a medical treatment implement according to a first embodiment.

FIG. 1 is a diagram illustrating the configuration of a medical treatment implement 1 according to the present embodiment. As illustrated in FIG. 1, the medical treatment implement 1 has a holdable housing 3 and a tubular sheath (an elongated shaft) 5 connected to the housing 3. The sheath 5 extends along a longitudinal axis (central axis) C. Here, the direction along the longitudinal axis C is defined as the longitudinal axis direction. One end in the longitudinal axis direction is defined as the distal side (arrow C1 side in FIG. 1), and the opposite side from the distal side is defined as the proximal side (arrow C2 side in FIG. 1). The sheath 5 is extended along the longitudinal axis C from the proximal side to the distal side and connected to the distal side of the housing 3. The housing 3 includes a distal end outer surface 3A, which forms the distal end of the housing 3, and a proximal end outer surface 3B, which forms the proximal end of the housing 3. The distal end outer surface 3A is directed toward the distal side, while the proximal end outer surface 3B is directed toward the proximal side.

The sheath 5 is installed to be rotatable about the longitudinal axis C with respect to the housing 3. The sheath 5 has a pipe 10 and a rotation control knob 18, which is a rotation control input unit attached to the proximal end portion of the pipe 10. The proximal end portion of the pipe 10 is inserted from the distal side into the rotation control knob 18 and fixed to the rotation control knob 18. Further, the pipe 10 is extended from the rotation control knob 18 toward the distal side. Further, an end effector 7 for treating a treatment target is attached to the distal side of the sheath 5 (the pipe 10). When the rotation control knob 18 is rotated about the longitudinal axis C with respect to the housing 3, the operation of rotating the end effector 7 about the longitudinal axis C is input through the rotation control knob 18. The operation input through the rotation control knob 18 causes a driving force (rotational driving force) to be transmitted to the sheath 5, and the sheath 5 rotates about the longitudinal axis C (i.e. together with the rotation control knob 18 and the pipe 10) with respect to the housing 3.

Figure 2:
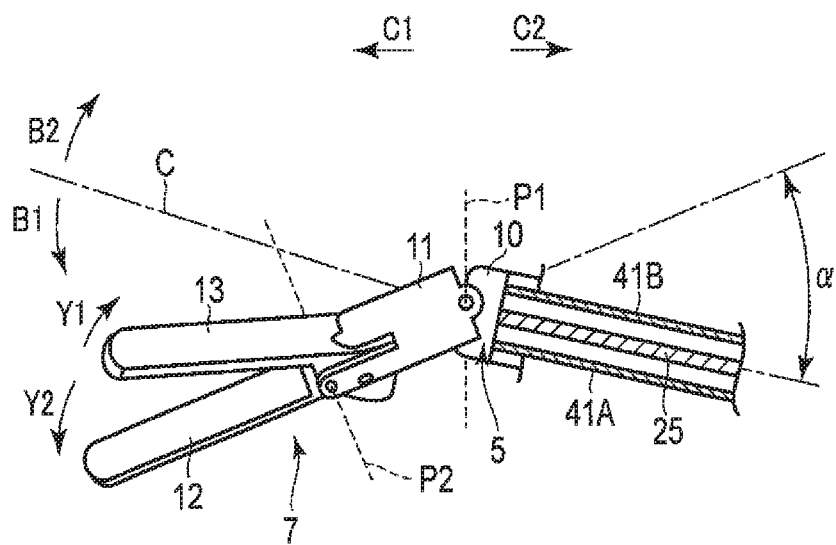
FIG. 2 illustrates a schematic perspective view of the configuration of an end effector according to the first embodiment.

FIG. 2 is a diagram illustrating the configuration of the end effector 7. As illustrated in FIG. 2, the end effector 7 has an effector base 11 attached to the sheath 5 (the pipe 10), a first gripping piece 12 fixed to the effector base 11 and a second gripping piece 13 pivotably connected to the effector base 11. The effector base 11 is attached to the sheath 5 such that the effector base 11 is pivotable about a pivot axis (articulation pivot axis) P1 with respect to the sheath 5. The pivot axis P1 extends along a direction that intersects with (being substantially perpendicular to) the longitudinal axis C direction of the sheath 5. As the end effector 7 including the effector base 11 pivots about the pivot axis P1 with respect to the sheath 5, the end effector 7 articulates with respect to the sheath 5, as denoted by an arrow B1 and an arrow B2 in FIG. 2. The articulation of the end effector 7 causes a change in an articulation angle (angle) α of the end effector 7 with respect to the longitudinal axis C of the sheath 5.

The second gripping piece 13 can be pivoted about a pivot axis (opening/closing pivot axis) P2 with respect to the effector base 11. The pivot axis P2 extends along a direction which intersects with (being substantially perpendicular to) a longitudinal axis C direction and also intersects with (being substantially perpendicular to) the direction in which the pivot axis P1 extends. When the second gripping piece 13 pivots about the pivot axis P2, the space between the first gripping piece 12 and the second gripping piece 13 increases or decreases in the end effector 7. More specifically, when the second gripping piece 13 pivots, the end effector 7 opens or closes, as denoted by an arrow Y1 and an arrow Y2 in FIG. 2. Both the first gripping piece 12 and the second gripping piece 13 may be attached to be pivotable with respect to the effector base 11 (e.g. about the pivot axis P2). In this case, the first gripping piece 12 and the second gripping piece 13 are moved away from or toward each other by pivoting the first gripping piece 12 and the second gripping piece 13 so as to open or close the end effector 7. In the present embodiment, a treatment target, such as a body tissue, is grasped between the first gripping piece 12 and the second gripping piece 13 in order to treat the treatment target.

As illustrated in FIG. 1, the housing 3 has a housing main body 15, which is extended along the longitudinal axis C, and a grip (fixed handle) 16, which is extended from the housing main body 15 in a direction away from the longitudinal axis C. The sheath 5 formed of the pipe 10 and the rotation control knob 18 is connected to the housing main body 15 from the distal side. A lever (movable handle) 17 is pivotably attached to the housing 3. The lever 17 is positioned on the side where a grip 16 is positioned with respect to the longitudinal axis C, and positioned on the distal side with respect to the grip 16 in the present embodiment. As the lever 17 pivots with respect to the housing 3 and the lever 17 opens or closes with respect to the grip 16, the operation for opening or closing the end effector 7 as described above is input through the lever 17, which is an opening/closing control input unit.

Further, an articulation control dial 20, which is an articulation control input unit, is attached to the housing 3. The articulation control dial 20 is positioned on the proximal side apart from the rotation control knob 18. An operation for articulating the end effector 7 as described above is input through the articulation control dial 20.

Further, control buttons 19A, 19B, which are energy control input sections, are attached to the housing 3 (a housing distal end outer surface 3A in the present embodiment). Applying an operation input through the control button 19A supplies a high-frequency electric energy to, for example, the gripping pieces 12 and 13. Thus, a high-frequency current is applied to the treatment target held between the gripping pieces 12 and 13 to treat the treatment target. Applying an operation input through the control button 19B supplies electric energy to, for example, a heating element (not illustrated) provided in the end effector 7. Thus, the heat generated by the heating element is used to treat the treatment target. The energy supplied to the end effector 7 is not limited to the foregoing energy. Other types of energy used for treatment may be supplied to the end effector 7 by applying an operation input through the control button 19A or 19B.

Figure 3:
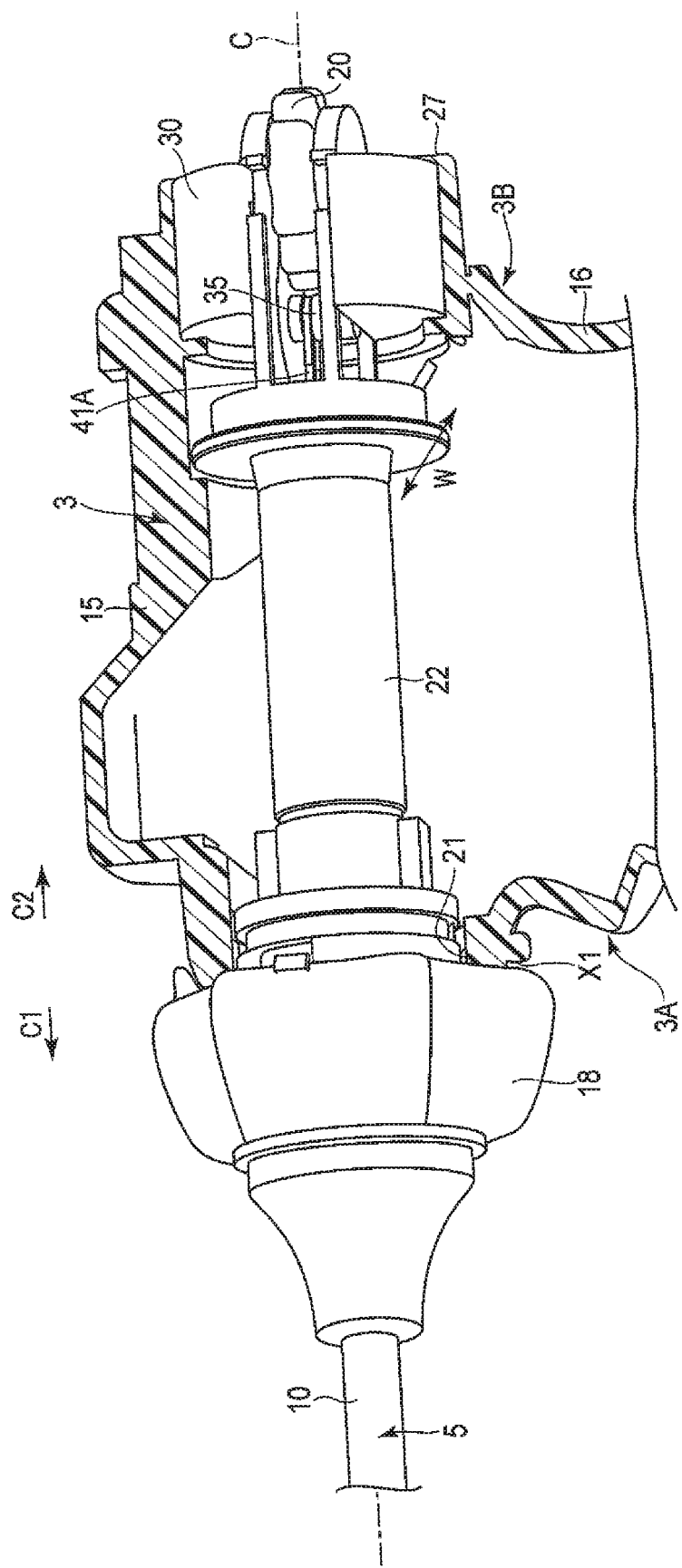
FIG. 3 illustrates a schematic perspective view of the internal configuration of a housing according to the first embodiment.
Figure 4:
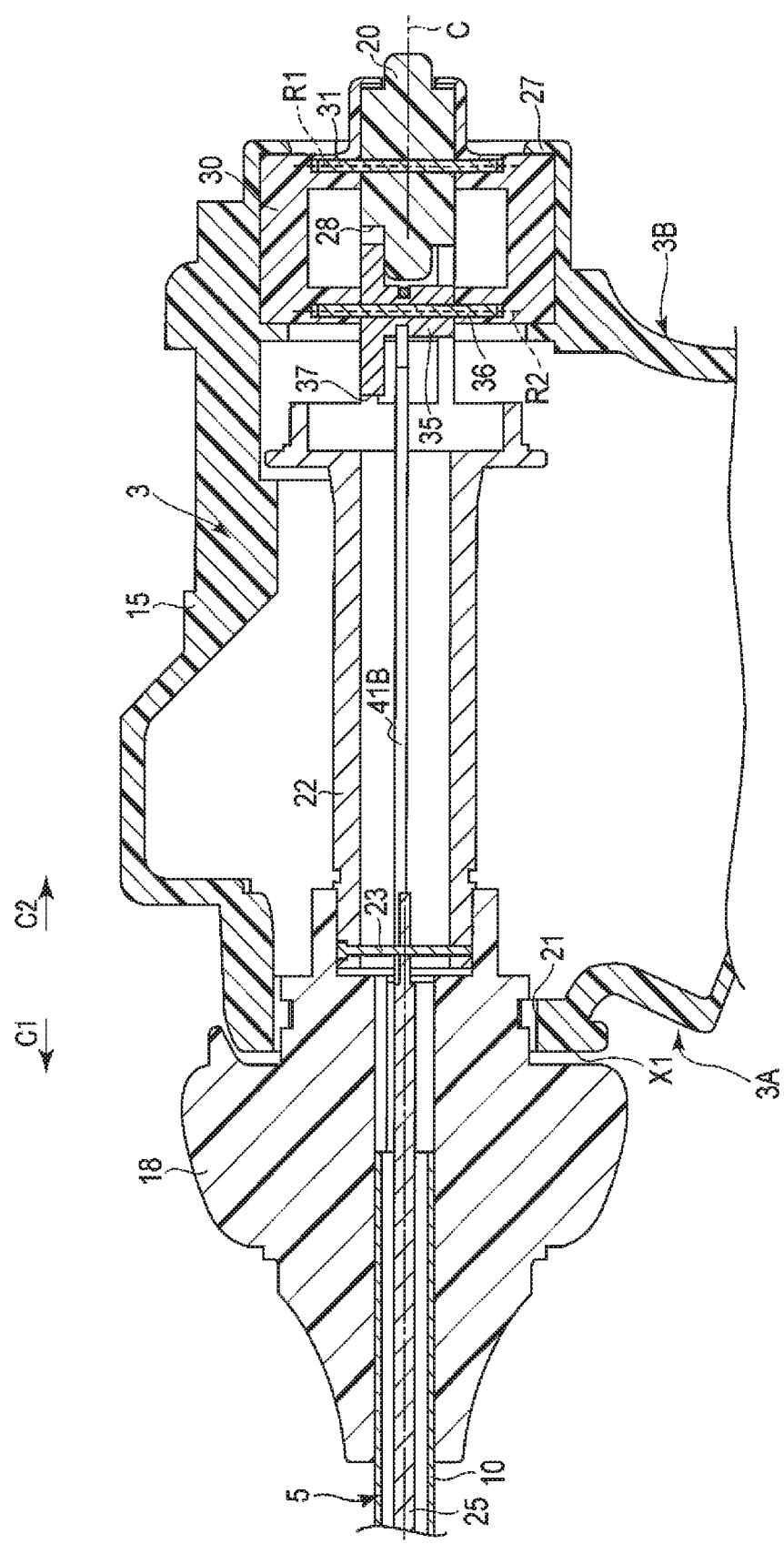
FIG. 4 illustrates a schematic sectional view of the internal configuration of the housing according to the first embodiment, which is observed at a section substantially perpendicular to the direction of the width of the housing.
Figure 5:
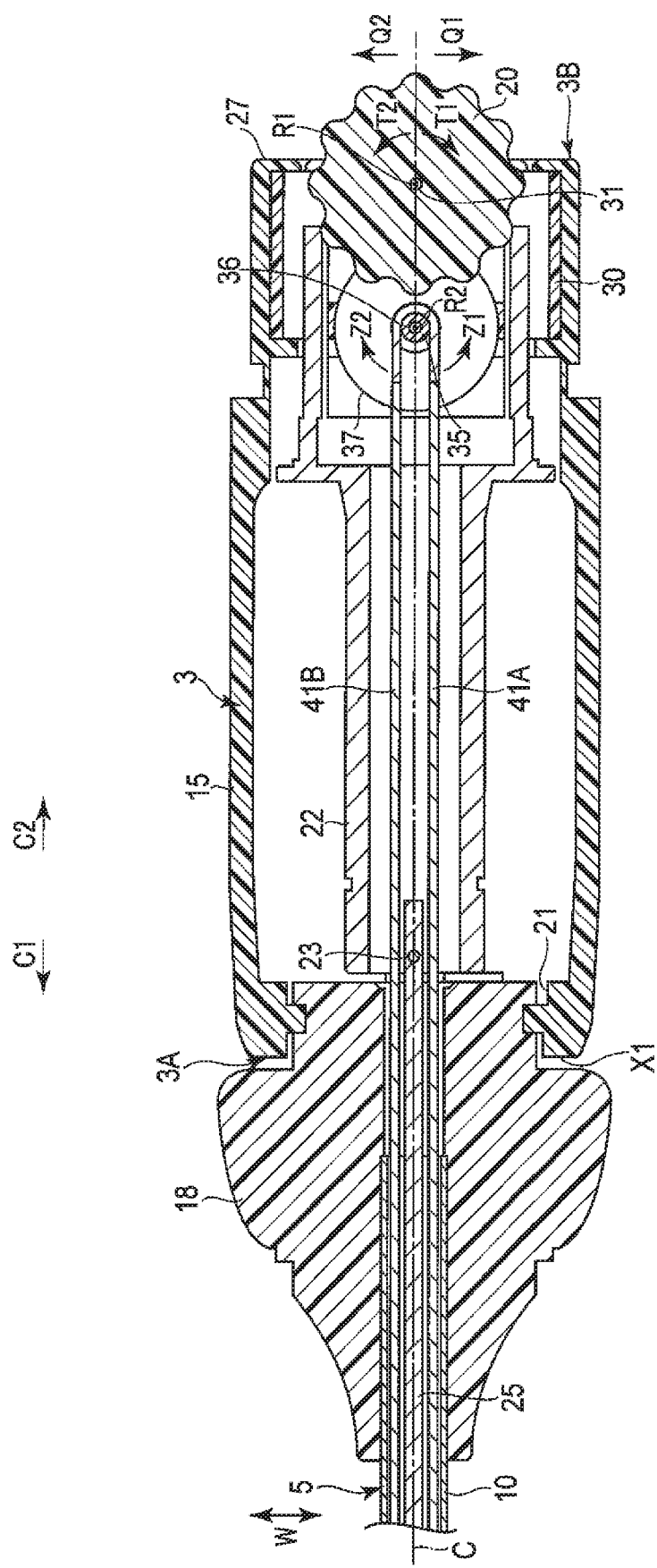
FIG. 5 illustrates a schematic sectional view of the internal configuration of the housing according to the first embodiment, which is observed at a section substantially parallel to the direction of a longitudinal axis and substantially parallel to the direction of the width of the housing.

FIG. 3 to FIG. 5 are diagrams illustrating the internal configuration of the housing main body 15 of the housing 3 and the internal configuration of the rotation control knob 18. FIG. 3 is a perspective view, FIG. 4 illustrates a section substantially perpendicular to (intersecting with) the width direction (the direction of an arrow W in FIG. 3 and FIG. 5) of the housing 3, and FIG. 5 illustrates a section which is substantially parallel to the longitudinal axis C direction and which is also substantially parallel to the width direction of the housing 3.

As illustrated in FIG. 3 to FIG. 5, in the housing 3 (the housing main body 15), an opening 21 that opens toward the distal side (on an arrow C1 side in FIG. 3 to FIG. 5) is formed at a reference position X1. The sheath 5 (the assembly composed of the rotation control knob 18 and the pipe 10) is inserted into the housing 3 from the distal side through the opening 21 at the reference position X1 and installed to the housing 3. Further, the sheath 5 is connected to the distal side of the housing 3 such that the sheath 5 projects toward the distal side from the reference position X1 of the housing 3 (the housing main body 15). In the present embodiment, the reference position X1 is on the distal end outer surface 3A of the housing 3 and at the distal end of the housing main body 15. According to the present embodiment, therefore, the sheath 5 (the assembly composed of the rotation control knob 18 and the pipe 10) is inserted into the housing main body 15 from the distal end outer surface 3A of the housing 3.

In the housing 3 (the housing main body 15), a tubular movable member 22 is attached to the sheath 5 (the rotation control knob 18) from the proximal side (an arrow C2 side in FIG. 3 to FIG. 5). The movable member 22 is extended along the longitudinal axis C and is capable of moving along the longitudinal axis C with respect to the housing 3 and the sheath 5 (the rotation control knob 18 and the pipe 10). However, the rotation of the movable member 22 about the longitudinal axis C with respect to the sheath 5 is restricted. In the housing 3, the lever 17 is connected to the movable member 22 through the intermediary of a slider (not illustrated) disposed on the outer peripheral surface of the movable member 22. The movable member 22 is connected to the lever 17 such that the movable member 22 is rotatable about the longitudinal axis C with respect to the lever 17. Further, inside the housing 3, a drive shaft 25, which is an opening/closing drive member, is fixed to the movable member 22 through the intermediary of a connection member 23. The drive shaft 25 is extended along the longitudinal axis C from the inside of the movable member 22 toward the distal side through the inside of the sheath 5.

When an operation input is supplied through the rotation control knob 18, the rotation control knob 18 rotates about the longitudinal axis C, thus transmitting a driving force (rotational driving force) to the movable member 22 attached to the rotation control knob 18. This causes the movable member 22 and the drive shaft 25 to rotate, with respect to the housing 3, about the longitudinal axis C together with the sheath 5 (the pipe 10) attached to the rotation control knob 18. Since the sheath 5 is fixed to the rotation control knob 18, the driving force (rotational driving force) is transmitted to the movable member 22 through the intermediary of the rotation control knob 18 when the sheath 5 is rotated. Further, the movable member 22 and the drive shaft 25 move along the longitudinal axis C with respect to the sheath 5 and the housing 3 when an operation input is supplied to release or squeeze the lever 17 with respect to the grip 16.

As illustrated in FIG. 2, the drive shaft 25 extended through the inside of the sheath 5 has one end (the distal end) thereof connected to the second gripping piece 13 of the end effector 7. As the lever 17 is released or squeezed with respect to the grip 16, the movable member 22 and the drive shaft 25 move along the longitudinal axis C, and the second gripping piece 13 pivots about the pivot axis P2, thus opening or closing the end effector 7 as described above. Further, according to the present embodiment, the drive shaft 25 is rotatable about the longitudinal axis C together with the sheath 5 (the rotation control knob 18 and the pipe 10). Hence, in response to an operation input supplied through the rotation control knob 18, the end effector 7 rotates about the longitudinal axis C with respect to the housing 3 together with the sheath 5 and the drive shaft 25. As the end effector 7 rotates about the longitudinal axis C, the angular position of the end effector 7 about the longitudinal axis C with respect to the housing 3 changes.

Further, as the end effector 7 rotates, the pivot axes P1 and P2 also rotate about the longitudinal axis C with respect to the housing 3, and the extending directions of the pivot axes P1 and P2 change accordingly. Thus, the articulation direction of the articulating movement of the end effector 7 (the directions of the arrow B1 and the arrow B2 in FIG. 2) changes and the opening/closing direction (the directions of the arrow Y1 and the arrow Y2 in FIG. 2) of the opening/closing movement thereof also changes. However, the articulation direction of the end effector 7 intersects with (being substantially perpendicular to) the direction of the longitudinal axis C, and the opening/closing direction of the end effector 7 intersects with (being substantially perpendicular to) the direction of the longitudinal axis C and also intersects with (being substantially perpendicular to) the articulation direction of the articulation movement, regardless of the angular position of the end effector 7 about the longitudinal axis C.

As illustrated in FIG. 3 to FIG. 5, the articulation control dial 20, which is an articulation control input unit, is attached to the housing 3 through the intermediary of a rotation base 30, which is a base member. The rotation base 30 and the articulation control dial 20 are positioned closer to the proximal side than the reference position X1 (the distal end outer surface 3A in the present embodiment) of the housing 3, at which the opening 21 is formed. In the present embodiment, the rotation base 30 and the articulation control dial 20 are attached to an installation outer surface 27, which is directed to the proximal side in the housing main body 15 (the outer surface thereof). The rotation base 30 and the articulation control dial 20 are rotatable about the longitudinal axis C with respect to the installation outer surface 27, i.e. the housing 3. Further, according to the present embodiment, the installation outer surface 27 forms the proximal end outer surface 3B of the housing 3 and forms the proximal end of the housing main body 15.

The articulation control dial 20 is attached to the rotation base 30 through the intermediary of a support shaft 31. The articulation control dial 20 is rotatable about a rotation axis R1, which is the central axis of the support shaft 31, with respect to the rotation base 30. The articulation control dial 20 is rotated about the rotation axis R1 to supply an operation input for articulating the end effector 7. At this time, the directions denoted by an arrow Q1 and an arrow Q2 in FIG. 5 are the directions of the operation of the articulation control dial 20. The rotation axis R1 is extended along the direction that intersects with (being substantially perpendicular to) the longitudinal axis C direction of the sheath 5. Further, the articulation control dial 20 has a gear 28 formed over the whole circumference around the rotation axis R1. In the present embodiment, the gear 28 is disposed inside the housing 3 without being exposed outside the housing 3.

A pulley 35 is installed to the rotation base 30 through the intermediary of a support shaft 36. In the present embodiment, the pulley 35 is positioned inside the housing main body 15 and positioned at the distal side with respect to the articulation control dial 20. The pulley 35 is rotatable about a rotation axis R2, which is the central axis of the support shaft 36, with respect to the rotation base 30. The rotation axis R2 is extended to intersect with (being substantially perpendicular to) the longitudinal axis C direction of the sheath 5 and also along the direction substantially parallel to the rotation axis R1. Further, the pulley 35 has a gear 37 formed over the whole circumference around the rotation axis R2. The gear 37 meshes with the gear 28 of the articulation control dial 20.

The proximal ends (one ends) of articulation wires 41A, 41B, which are articulation drive members (drive members), are connected to the pulley 35. The articulation wires 41A, 41B are extended along the longitudinal axis C toward the distal side through the inside of the movable member 22 and the inside of the sheath 5. As illustrated in FIG. 2, the distal ends (the other ends) of the articulation wires 41A, 41B are connected to an effector base 11 of the end effector 7. As the articulation control dial 20 rotates about the rotation axis R1 with respect to the rotation base 30 in response to an operation input, the pulley 35 rotates about the rotation axis R2. Thus, the articulation wires 41A, 41B, which are the articulation drive members, are driven, and the articulation wires 41A, 41B move along the longitudinal axis C with respect to the sheath 5. As the articulation wires 41A, 41B move, the end effector 7 articulates with respect to the sheath 5, as described above.

For example, if the articulation control dial 20 is rotated to one side (to the side denoted by an arrow T1 in FIG. 5) by the operation input for moving the articulation control dial 20 to one side of the operational direction (to the side denoted by an arrow Q1 in FIG. 5), then the pulley 35 rotates to one side (to the side denoted by an arrow Z1 in FIG. 5) of the rotational direction. Thus, the articulation wire 41A moves to the proximal side (to be tightened) while the articulation wire 41B moves to the distal side (to be loosened), causing the end effector 7 to articulate to one side (to the side denoted by the arrow B1 in FIG. 2) of the articulation direction with respect to the sheath 5 (the longitudinal axis C). Meanwhile, if the articulation control dial 20 is moved to the other side (to the side denoted by an arrow T2 in FIG. 5) by the operation input for moving the articulation control dial 20 to the other side of the operational direction (to the side denoted by an arrow Q2 in FIG. 5), then the pulley 35 rotates to the other side (to the side denoted by an arrow Z2 in FIG. 5) of the rotational direction. Thus, the articulation wire 41B moves to the proximal side while the articulation wire 41A moves to the distal side, causing the end effector 7 to articulate to the other side (to the side denoted by the arrow B2 in FIG. 2) of the articulation direction with respect to the sheath 5 (the longitudinal axis C).

Here, a state in which the angle of the end effector 7 with respect to the sheath 5 is zero degrees (a position at which the end effector 7 is not articulated with respect to the sheath 5) is defined as the neutral state. According to the present embodiment, the ratio of an articulation angle α (the amount of articulation) of the end effector 7 from the neutral state with respect to the amount of rotation (the manipulated variable based on an operation input) of the articulation control dial 20 from the neutral state is set on the basis of the gear ratio between the gear 28 and the gear 37. Hence, at the time of manufacturing the medical treatment implement 1, the ratio of the articulation angle α of the end effector 7 from the neutral state with respect to the amount of rotation of the articulation control dial 20 from the neutral state is adjusted by adjusting the gear ratio between the gear 28 and the gear 37.

Further, inside the housing main body 15, the rotation base 30 is connected to the movable member 22 from the proximal side. The movable member 22 is movably connected along the longitudinal axis C with respect to the rotation base 30. Further, the rotations of the movable member 22 and the rotation base 30 about the longitudinal axis C with respect to each other are restricted. Therefore, the movable member 22, which connects the sheath 5 (the rotation control knob 18 and the pipe 10) and the articulation control dial 20 (the rotation base 30), is rotatable about the longitudinal axis C together with the sheath 5 and the articulation control dial 20 and is movable along the longitudinal axis C with respect to the sheath 5 and the articulation control dial 20.

With the foregoing configuration, the end effector 7, the sheath 5, the movable member 22, and the drive shaft 25 rotate about the longitudinal axis C in response to the operation input through the rotation control knob 18, thus transmitting the driving force (the rotational driving force) to the rotation base 30 from the sheath 5 through the movable member 22. This causes the rotation base 30 to rotate about the longitudinal axis C together with the end effector 7, the sheath 5, the movable member 22, and the drive shaft 25 with respect to the installation outer surface 27. At this time, the driving force (the rotational driving force) is transmitted from the rotation base 30 also to the articulation control dial 20, the pulley 35, and the support shafts 31, 36, which are installed to the rotation base 30. The articulation control dial 20, the pulley 35, and the support shafts 31, 36 rotate about the longitudinal axis C together with the rotation base 30 with respect to the installation outer surface 27. In other words, according to the present embodiment, as the sheath 5 rotates about the longitudinal axis C with respect to the housing 3 in response to the operation input supplied through the rotation control knob 18, which is the rotation control input unit, the articulation control dial 20, which is the articulation control input unit, and the end effector 7 also rotate about the longitudinal axis C together with the sheath 5 with respect to the housing 3. Further, as the end effector 7 and the pulley 35 rotate about the longitudinal axis C in response to an operation input supplied through the rotation control knob 18, the articulation wires 41A, 41B connecting the end effector 7 and the pulley 35 also rotate about the longitudinal axis C.

Further, the rotation of the rotation base 30 and the members, such as the articulation control dial 20, installed to the rotation base 30 causes the rotation axes R1, R2 to rotate about the longitudinal axis C with respect to the housing 3, thus changing the extending directions of the rotation axes R1, R2. This in turn changes the rotational directions of the pulley 35 (the directions denoted by the arrow Z1 and the arrow Z2 in FIG. 5) and the rotational directions of the articulation control dial 20 (the directions denoted by the arrow T1 and the arrow T2 in FIG. 5), thus changing the operational directions (the directions denoted by the arrow Q1 and the arrow Q2 in FIG. 5) of the operation input to the articulation control dial 20. However, the operational direction of the articulation control dial 20 intersects with (being substantially perpendicular to) the longitudinal axis C and intersects with (being substantially perpendicular to) the extending directions of the rotation axes R1, R2, regardless of the angular positions of the rotation base 30 and the articulation control dial 20 about the longitudinal axis C.

As described above, according to the present embodiment, the sheath 5, the end effector 7, and the articulation control dial 20 rotate together about the longitudinal axis C in response to an operation input supplied through the rotation control knob 18. Hence, if the angular position of the end effector 7 about the longitudinal axis C changes due to the rotation of the end effector 7, then the angular position of the articulation control dial 20 about the longitudinal axis C changes according to the change in the angular position of the end effector 7. Therefore, when an operation input is supplied through the rotation control knob 18, the operational directions of the articulation control dial 20 (the directions denoted by the arrow Q1 and the arrow Q2 in FIG. 5) change according to the changes in the articulation directions of the end effector 7 (the directions denoted by the arrow B1 and the arrow B2 in FIG. 2). For example, from a state in which the articulation direction of the end effector 7 and the operational direction of the articulation control dial 20 are substantially parallel, the end effector 7 is rotated about the longitudinal axis C by an operation input through the rotation control knob 18. At this time, the articulation control dial 20 rotates about the longitudinal axis C together with the end effector 7, so that the state, in which the articulation direction of the end effector 7 and the operational direction of the articulation control dial 20 are substantially parallel, is maintained even when the angular position of the end effector 7 about the longitudinal axis C changes. In other words, according to the present embodiment, even when an operation input is supplied through the rotation control knob 18, the end effector 7 and the articulation control dial 20 rotate together about the longitudinal axis C without changing the relative relationship between the articulation direction of the end effector 7 and the operational direction of the articulation control dial 20.

Further, according to the present embodiment, regardless of the angular position of the articulation control dial 20 about the longitudinal axis C, the longitudinal axis C of the sheath 5 passes the articulation control dial 20. Hence, in the state in which the articulation control dial 20 is rotating about the longitudinal axis C together with the sheath 5 in response to the operation input supplied through the rotation control knob 18, the articulation control dial 20 is located at the position where the longitudinal axis C of the sheath 5 passes. Therefore, even when the articulation control dial 20 rotates together with the sheath 5, the position of the articulation control dial 20 on a plane perpendicular to the longitudinal axis C hardly changes.

A description will now be given of the operation and effect of the medical treatment implement 1 according to the present embodiment. When performing a treatment by using the medical treatment implement 1, the end effector 7 is inserted into a body cavity, such as an abdominal cavity. Then, the end effector 7 is brought to a treatment target. At this time, the end effector 7 is rotated about the longitudinal axis C by supplying an operation input through the rotation control knob 18 or the end effector 7 is articulated with respect to the sheath 5 by an operation input through the articulation control dial 20 so as to place the end effector 7 at a position that allows the treatment target to be easily gripped. Then, the treatment target is positioned between the pair of the gripping pieces 12, 13, and the end effector 7 is closed by supplying an operation input through the lever 17. Thus, the treatment target is held between the gripping pieces 12, 13. In this state, an operation input is given through the control button 19A or 19B to supply energy to the end effector 7, thereby treating the treatment target by using the energy (treatment energy).

According to the present embodiment, the sheath 5, the end effector 7, and the articulation control dial 20 rotate together about the longitudinal axis C in response to an operation input supplied through the rotation control knob 18. Hence, even when the angular position of the end effector 7 about the longitudinal axis C with respect to the housing 3 changes, the relative angular position of the articulation control dial 20 about the longitudinal axis C with respect to the sheath 5 and the end effector 7 remains unchanged. In other words, even when an operation input is given through the rotation control knob 18, the end effector 7 and the articulation control dial 20 rotate together about the longitudinal axis C without changing the relative relationship between the articulation directions of the end effector 7 (the directions denoted by the arrow B1 and the arrow B2 in FIG. 2) and the operational directions of the articulation control dial 20 (the directions denoted by the arrow Q1 and the arrow Q2 in FIG. 5). This enables the operator to easily know the articulation direction of the end effector 7 regardless of the angular position of the end effector 7 about the longitudinal axis C.

Further, in a state in which the housing 3 is held by one hand (e.g. the right hand), the palm is in contact with the grip 16 (the proximal end outer surface 3B) from the proximal side, and the middle finger, the ring finger, and the little finger are placed on the lever 17. Further, the forefinger is used to supply an operation input for rotating the rotation control knob 18 and to also supply an operation input to the control button 19A or 19B. According to the present embodiment, the articulation control dial 20, which is the articulation operation input unit, is positioned more closely to the proximal side than the reference position X1, which is the position at which the sheath 5 (the pipe 10 and the rotation control knob 18) projects toward the distal side from the housing 3 (the housing main body 15). Hence, when the housing 3 is held as mentioned above, the articulation control dial 20 can be easily rotated thereby to allow an operation input to be easily given by a thumb through the articulation control dial 20, regardless of the angular position of the end effector 7 about the longitudinal axis C. Thus, an operation input can be easily given using the articulation control dial 20 only by the hand (i.e. one hand) holding the housing 3, independently of the angular position of the end effector 7 about the longitudinal axis C.

Further, in the present embodiment, the articulation control dial 20 is positioned apart on the proximal side from the rotation control knob 18 connected to the distal side of the housing 3. This arrangement makes it easier to enter an operation input through the articulation control dial 20 by the thumb when the housing 3 is being held as described above. Further, in the present embodiment, the articulation control dial 20 is installed to the installation outer surface 27 facing the proximal side in the housing 3, and the installation outer surface 27 forms the proximal end outer surface 3B of the housing 3. This arrangement makes it easier to enter an operation input through the articulation control dial 20 by the thumb when the housing 3 is being held as described above. Further, the articulation control dial 20 and the rotation base 30 are installed to the proximal end outer surface 3B of the housing 3, thus properly securing the space for placing the movable member 22 and the space for providing the articulation wires 41A, 41B inside the housing 3.

Further, according to the present embodiment, in the state in which the articulation control dial 20 is rotating about the longitudinal axis C together with the sheath 5 in response to an operation input supplied through the rotation control knob 18, the articulation control dial 20 is located at the position that the longitudinal axis C of the sheath 5 passes, and the position of the articulation control dial 20 on a plane perpendicular to the longitudinal axis C hardly changes. Since the position of the articulation control dial 20 on the plane perpendicular to the longitudinal axis C hardly changes, it is further easier to enter an operation input through the articulation control dial 20 independently of the angular position of the end effector 7 about the longitudinal axis C.

As described above, the present embodiment can provide the medical treatment implement 1 that ensures ease of operation for articulating the end effector 7 with respect to the sheath 5 regardless of the angular position of the end effector 7 about the longitudinal axis C.

The part of the rotation base 30 that projects from the housing 3 may be rotated about the longitudinal axis C by, for example, the thumb of the right hand thereby to rotate the sheath 5 and the end effector 7 about the longitudinal axis C with respect to the housing 3.

Modification Example

Figure 6:
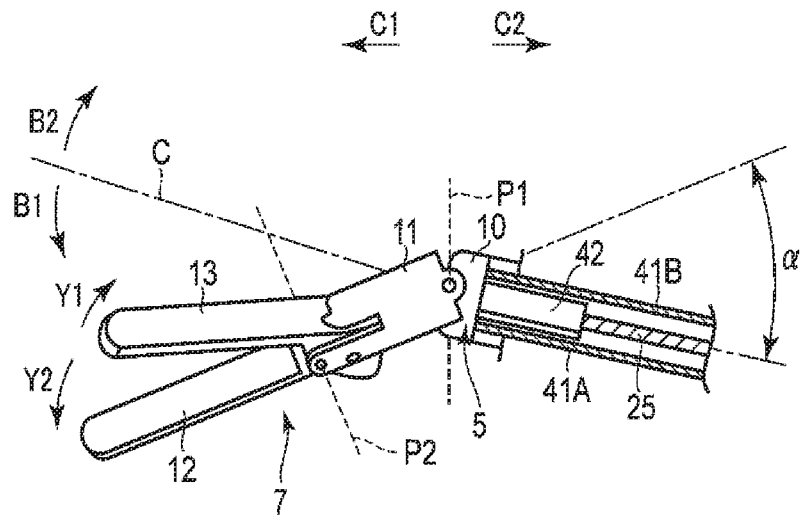
FIG. 6 illustrates a schematic perspective view of the configuration of an end effector according to a first modification example.

In a first modification example illustrated in FIG. 6, the distal end of a drive shaft 25 is connected to a plate member 42 formed of an elastic material, and the plate member 42 is connected to an end effector 7 (a second gripping piece 13). The plate member 42 is movable together with the drive shaft 25 along a longitudinal axis C with respect to a sheath 5. Further, as the drive shaft 25 and the plate member 42 move together along the longitudinal axis C, the end effector 7 opens or closes as described above. In the present modification example, the position at which the drive shaft 25 is connected to the plate member 42 (the distal end of the drive shaft 25) is on the proximal side with respect to a pivot axis P1 of the articulation operation of the end effector 7 with respect to the sheath 5 regardless of whether gripping pieces 12, 13 of the end effector 7 are opened or closed (i.e. the positions of the drive shaft 25 and the plate member 42 in a longitudinal axis C direction). In other words, regardless of whether the gripping pieces 12, 13 of the end effector 7 are opened or closed, the distal end of the drive shaft 25 is positioned at the proximal side with respect to an articulating joint of the end effector 7.

In the present modification example having the configuration described above, even when the end effector 7 articulates with respect to the sheath 5, the hard drive shaft 25 will not be subjected to a large force, and the plate member 42 formed of an elastic material elastically deforms due to the force generated by the articulation operation of the end effector 7. Therefore, the articulation movement of the end effector 7 is not impeded by the drive shaft 25, thus enabling the end effector 7 to properly articulate with respect to the sheath 5.

Figure 7:
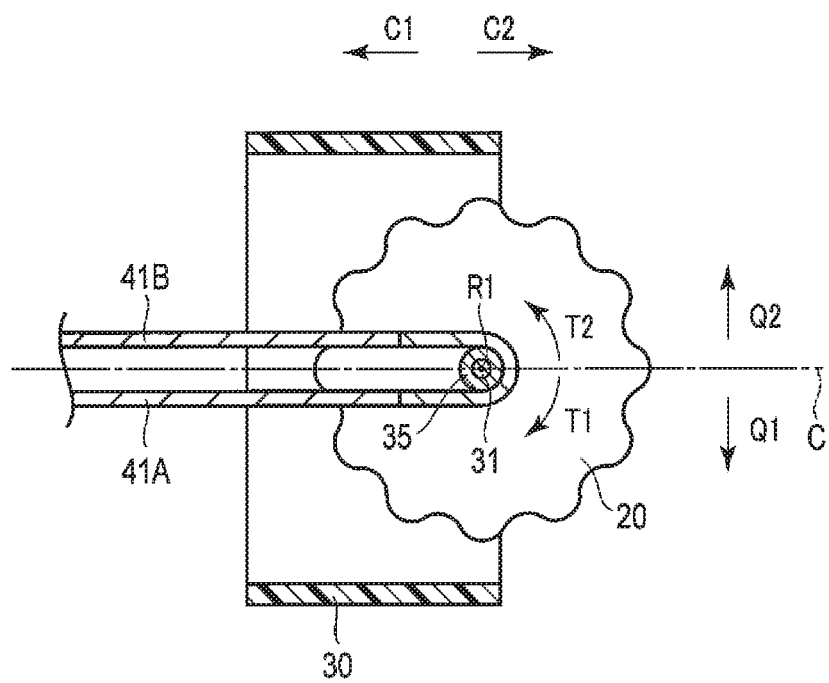
FIG. 7 illustrates a schematic sectional view of the configuration of an articulation control dial and the vicinity thereof according to a second modification example.

Further, in a second modification example illustrated in FIG. 7, a pulley 35, to which the proximal ends of articulation wires 41A, 41B are connected, is provided coaxially with an articulation control dial 20, which is an articulation operation input unit. The pulley 35 is rotatable about a rotation axis R1 together with the articulation control dial 20 with respect to a rotation base 30. Hence, in the present modification example, the gears 28 and 37 described in the first embodiment are not provided.

As with the first embodiment, in the present modification example, when a rotation control knob 18 is rotated about a longitudinal axis C, a driving force (rotational driving force) is transmitted to the rotation base 30 and the articulation control dial 20 through a movable member 22. This causes the rotation base 30, the articulation control dial 20, the pulley 35, and the articulation wires 41A, 41B to rotate about the longitudinal axis C together with a sheath 5 and an end effector 7 with respect to a housing 3. As with the first embodiment, therefore, even when the angular position of the end effector 7 about the longitudinal axis C changes, the end effector 7 and the articulation control dial 20 rotate together about the longitudinal axis C without changing the relative relationship between the articulation direction of the end effector 7 and the operational directions of the articulation control dial 20.

In the present modification example, as the articulation control dial 20 rotates about the rotation axis R1 with respect to the rotation base 30 in response to an operation input, the pulley 35 rotates about the rotation axis R1 together with the articulation control dial 20 with respect to the rotation base 30. This causes the articulation wires 41A, 41B to move along the longitudinal axis C with respect to the sheath 5, and the end effector 7 to articulate with respect to the sheath 5 as described above. For example, when the articulation control dial 20 is moved to one side (the side denoted by an arrow Q1 in FIG. 7) of the operational direction by supplying an operation input, the articulation control dial 20 and the pulley 35 rotate to one side (the side denoted by an arrow T1 in FIG. 7) of the rotational direction. Thus, the articulation wire 41B moves to the proximal side (to be tightened) while the articulation wire 41A moves to the distal side (to be loosened), causing the end effector 7 to articulate to the side denoted by the arrow B2 in FIG. 2 of the articulation direction with respect to the sheath 5. Meanwhile, if the articulation control dial 20 is rotated to the other side (to the side denoted by an arrow Q2 in FIG. 7) by an operation input, then the articulation control dial 20 and the pulley 35 rotate to the other side (to the side denoted by an arrow T2 in FIG. 7) of the rotational direction. Thus, the articulation wire 41A moves to the proximal side while the articulation wire 41B moves to the distal side, causing the end effector 7 to articulate to the side denoted by the arrow B1 in FIG. 2) with respect to the sheath 5.

Here, it is assumed that the articulation direction of the end effector 7 and the operational direction of the articulation control dial 20 are substantially parallel regardless of the angular position of the end effector 7 about the longitudinal axis C. In this case, according to the configuration of the first embodiment (the configuration illustrated in FIG. 3 to FIG. 5), the side of the operational direction of the articulation control dial 20 (the directions denoted by the arrow Q1 and the arrow Q2 in FIG. 5) to which the articulation control dial 20 moves in response to an operation input is the same as the side of the articulation direction of the end effector 7 (the directions denoted by the arrow B1 and the arrow B2 in FIG. 2) to which the end effector 7 articulates. In contrast to this, according to the configuration of the second modification example (the configuration illustrated in FIG. 7), the side of the operational direction of the articulation control dial 20 (the directions denoted by an arrow Q1 and an arrow Q2 in FIG. 7) to which the articulation control dial 20 moves in response to an operation input is opposite from the side of the articulation direction of the end effector 7 to which the end effector 7 is articulated. Hence, the relationship between the side to which the articulation control dial 20, which is the articulation operation input unit, is moved (the side to which the articulation control dial 20 is operated) in response to an operation input, and the side to which the end effector 7 is articulated by the articulation operation is determined according to the configuration for transmitting an operational force generated by an operation input supplied through the articulation control dial 20 to the articulation wires 41A, 41B. Therefore, the relationship between the side to which the articulation control dial 20 is operated by an operation input and the side to which the end effector 7 is articulated by the articulation operation is determined by designing the configuration for transmitting the operational force from the articulation control dial 20 to the articulation wires 41A, 41B at the time of manufacturing the medical treatment implement 1.

Figure 8:
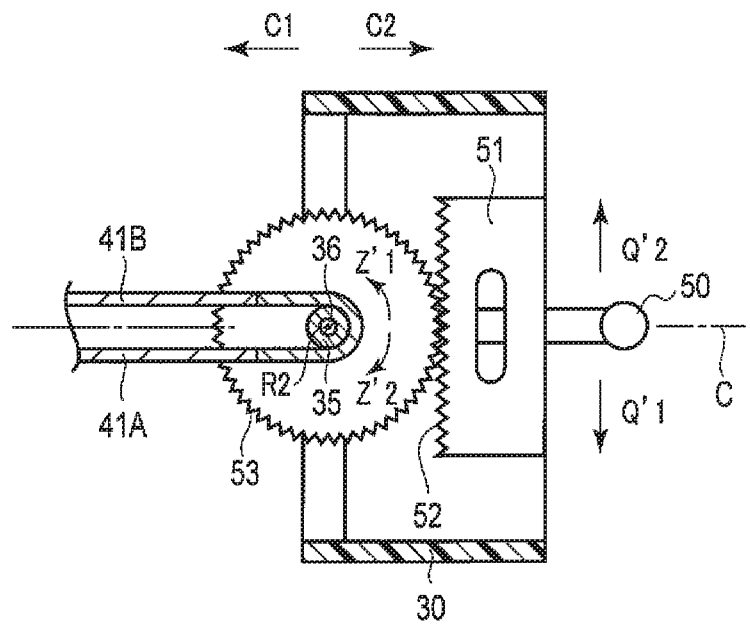
FIG. 8 illustrates a schematic sectional view of the configuration of an articulation control lever and the vicinity thereof according to a third modification example.

Further, in a third modification example illustrated in FIG. 8, as the articulation operation input unit, an articulation control lever 50 is provided in place of the articulation control dial 20. The articulation control lever 50 is installed to a rotation base 30 through the intermediary of a rack 51. The articulation control lever 50 is movable together with the rack 51 in the operational directions (the directions denoted by an arrow Q'1 and an arrow Q'2 in FIG. 8) of an operation input with respect to the rotation base 30. A gear section (linear gear section) 52 is formed on the rack 51 along the operational directions of the articulation control lever 50. As with the first embodiment, in the present modification example, a pulley 35 to which the proximal ends of articulation wires 41A, 41B are connected is rotatable about a rotation axis R2 with respect to the rotation base 30. In the present modification example, the pulley 35 has a gear section 53 formed over the whole circumference around the rotation axis R2, and the gear section 53 meshes with the gear section 52 of the rack 51.

As with the first embodiment, in the present modification example, as a rotation control knob 18 rotates about a longitudinal axis C, a driving force (rotational driving force) is transmitted to the rotation base 30 and the articulation control lever 50 through the intermediary of a movable member 22. This causes the rotation base 30, the articulation control lever 50, the pulley 35, and the articulation wires 41A, 41B to rotate about the longitudinal axis C together with a sheath 5 and an end effector 7 with respect to a housing 3. Hence, as with the first embodiment, even when the angular position of the end effector 7 about the longitudinal axis C changes, the end effector 7 and the articulation control lever 50 rotate together about the longitudinal axis C without changing the relative relationship between the articulation direction of the end effector 7 and the operational direction of the articulation control lever 50. In the present modification example, the operational direction of the articulation control lever 50 intersects with (being substantially perpendicular to) a longitudinal axis C direction and intersects with (being substantially perpendicular to) the extending direction of the rotation axis R2 regardless of the angular positions of the rotation base 30 and the articulation control lever 50 about the longitudinal axis C.

In the present modification example, as the articulation control lever 50 and the rack 51 move in the operational direction with respect to the rotation base 30 in response to an operation input, the pulley 35 rotates about the rotation axis R2. This causes the articulation wires 41A, 41B to move along the longitudinal axis C with respect to the sheath 5 and the end effector 7 to articulate with respect to the sheath 5 as described above. For example, when the articulation control lever 50 is moved to one side (the side denoted by the arrow Q'1 in FIG. 8) of the operational direction by supplying an operation input, the pulley 35 rotates to one side (the side denoted by an arrow Z'1 in FIG. 8) of the rotational direction. This in turn causes the articulation wire 41A to move to the proximal side, the articulation wire 41B to move to the distal side, and the end effector 7 to articulate with respect to the sheath 5 to the side denoted by an arrow B1 in FIG. 2. Meanwhile, when the articulation control lever 50 is moved to the other side (the side denoted by the arrow Q'2 in FIG. 8) of the operational direction by supplying an operation input, the pulley 35 rotates to the other side (the side denoted by an arrow Z'2 in FIG. 8) of the rotational direction. This in turn causes the articulation wire 41B to move to the proximal side, the articulation wire 41A to move to the distal side, and the end effector 7 to articulate with respect to the sheath 5 to the side denoted by an arrow B2 in FIG. 2.

Figure 9:
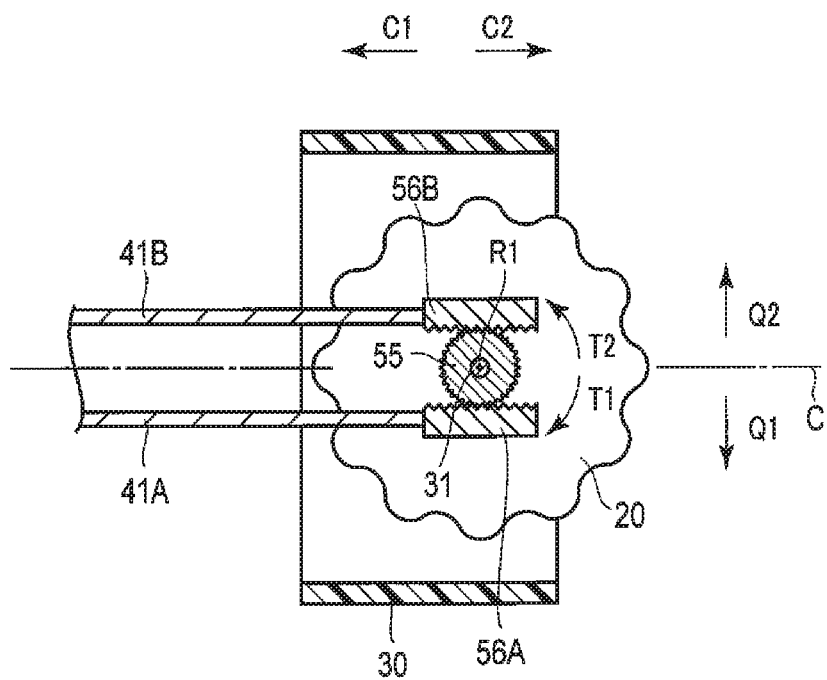
FIG. 9 illustrates a schematic sectional view of the configuration of an articulation control dial and the vicinity thereof according to a fourth modification example.

Further, in a fourth modification example illustrated in FIG. 9, a pinion gear 55 and rack gears 56A, 56B are provided in place of the pulley 35. The pinion gear 55 is provided coaxially with an articulation control dial 20 and is rotatable about a rotation axis R1 together with the articulation control dial 20 with respect to a rotation base 30. Further, the rack gears 56A, 56B mesh with the pinion gear 55, and each of the rack gears 56A and 56B has the proximal end of its corresponding articulation wire (41A or 41B) connected thereto. Each of the rack gears 56A and 56B is movable along a longitudinal axis C together with its corresponding articulation wire (41A or 41B).

As with the first embodiment, in the present modification example, when a rotation control knob 18 rotates about the longitudinal axis C, the driving force (rotational driving force) is transmitted to the rotation base 30 and the articulation control dial 20 through the intermediary of a movable member 22. This causes the rotation base 30, the articulation control dial 20, the pinion gear 55, the rack gears 56A, 56B, and the articulation wires 41A, 41B to rotate about the longitudinal axis C together with a sheath 5 and an end effector 7 with respect to a housing 3. Hence, as with the first embodiment, even when the angular position of the end effector 7 about the longitudinal axis C changes, the end effector 7 and the articulation control dial 20 rotate together about the longitudinal axis C without changing the relative relationship between the articulation direction of the end effector 7 and the operational direction of the articulation control dial 20.

In the present modification example, the articulation control dial 20 and the pinion gear 55 rotate about a rotation axis R1 in response to an operation input. This causes each of the articulation wires 41A and 41B to move along the longitudinal axis C together with its corresponding rack gear (56A or 56B) and the end effector 7 to articulate with respect to the sheath 5 as described above. For example, when the articulation control dial 20 is moved to one side (the side denoted by an arrow Q1 in FIG. 9) of the operational direction by supplying an operation input, the articulation control dial 20 and the pinion gear 55 rotate to one side (the side denoted by an arrow T1 in FIG. 9) of the rotational direction. This in turn causes the articulation wire 41A and the rack gear 56A to move to the proximal side, the articulation wire 41B and the rack gear 56B to move to the distal side, and the end effector 7 to articulate with respect to the sheath 5 to the side denoted by the arrow B1 in FIG. 2. Meanwhile, when the articulation control dial 20 is moved to the other side (the side denoted by an arrow Q2 in FIG.

9) of the operational direction by supplying an operation input, the articulation control dial 20 and the pinion gear 55 rotate to the other side (the side denoted by an arrow T2 in FIG. 9) of the rotational direction. This in turn causes the articulation wire 41B and the rack gear 56B to move to the proximal side, the articulation wire 41A and the rack gear 56A to move to the distal side, and the end effector 7 to articulate with respect to the sheath 5 to the side denoted by the arrow B2 in FIG. 2.

Further, in the embodiments and the like described above, the lever 17 is positioned at the distal side of the grip 16. However, in a modification example, the lever 17 is provided on the proximal side of the grip 16, and the lever 17 can be opened or closed with respect to the grip 16.

Figure 10:
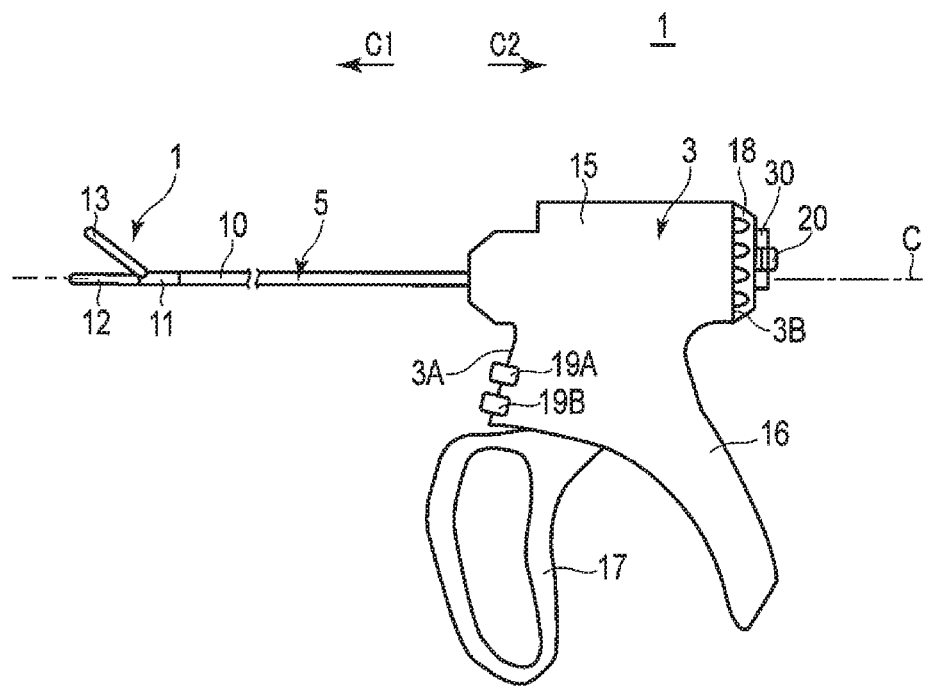
FIG. 10 illustrates a schematic diagram of a medical treatment implement according to a fifth modification example.
Figure 11:
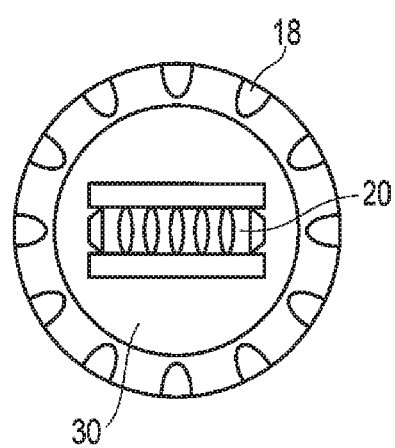
FIG. 11 illustrates a schematic diagram of a rotation control knob, a rotation base and an articulation control dial according to a fifth modification example, which are observed from a proximal side.
Figure 12:
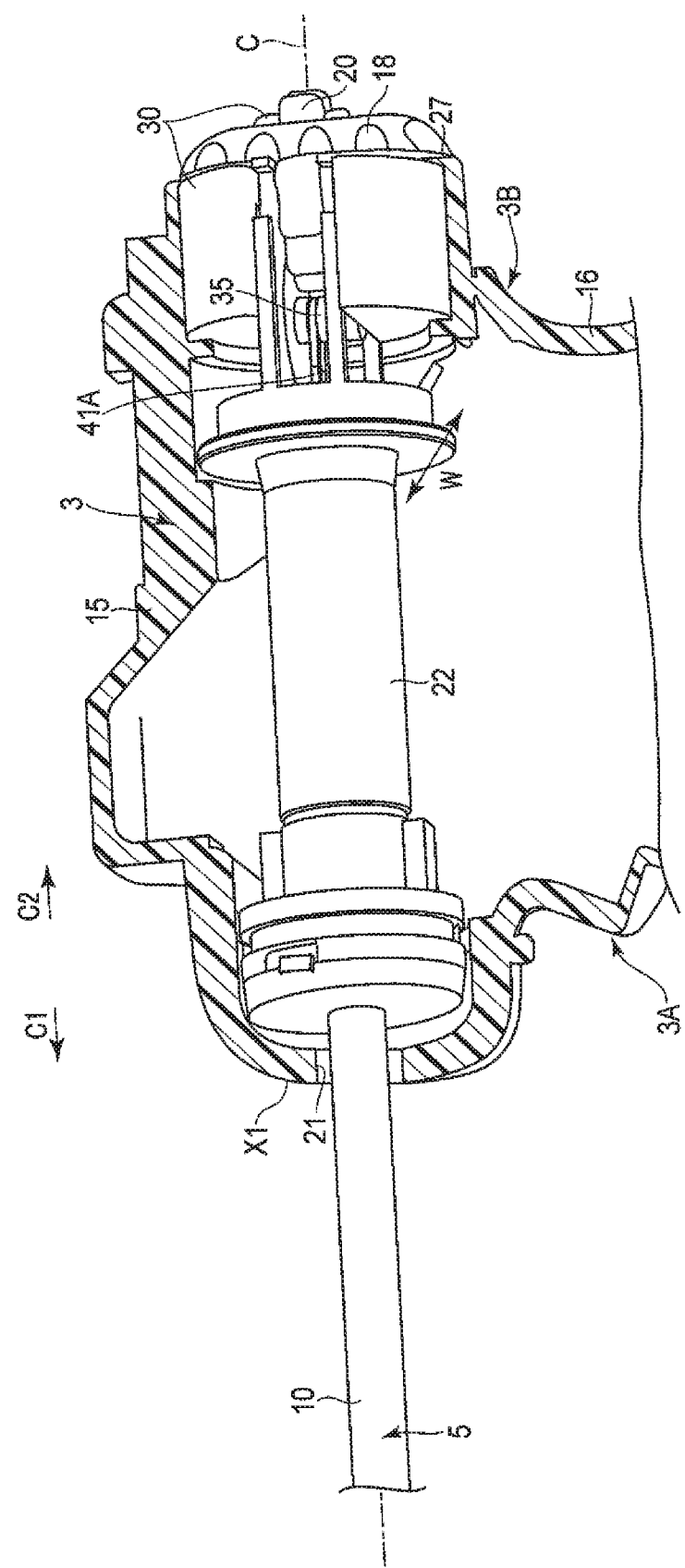
FIG. 12 illustrates a schematic perspective view of the internal configuration of a housing according to the fifth modification example.

Further, in a fifth modification example illustrated in FIG. 10 to FIG. 12, a rotation control knob 18 is installed to a housing 3 at a different position from that in the first embodiment. In the present modification example, the rotation control knob 18 is installed to an installation outer surface 27, which forms a part of a proximal end outer surface 3B of a housing 3. Further, the rotation control knob 18 is provided by being attached to a rotation base 30 at the proximal end portion of the housing 3. Hence, in the present modification example, the rotation control knob 18 is not made integral with a sheath 5 and not fixed to the sheath 5 (a pipe 10). However, in the present modification example also, a distal end outer surface 3A of the housing 3 has an opening 21 formed at a reference position X1, and the sheath 5 projects toward the distal side from the reference position X1 of the housing 3, as with the foregoing embodiments.

In the present modification example, the rotation control knob 18 is fixed to the outer rim of the rotation base 30. Inside the housing 3, the rotation base 30, to which the rotation control knob 18 is fixed, is installed to a movable member 22 from the proximal side, and the sheath 5 is installed to the movable member 22 from the distal side. Thus, when the rotation control knob 18 rotates about a longitudinal axis C, the rotation base 30 integrally rotates, and the movable member 22 and the sheath 5 rotate about the longitudinal axis C. In the present modification example, the movable member 22 is movable along the longitudinal axis C with respect to the sheath 5, the rotation control knob 18, and the rotation base 30.

In the present modification example, the rotation control knob 18 can be operated by, for example, the thumb of a hand holding the grip 16. Further, a groove may be formed in the surface of the rotation control knob 18 so as to make it easier for a finger to catch the rotation control knob 18.

Further, another modification example may include both a distal rotation control knob attached to a sheath 5, as with the rotation control knob 18 in the first embodiment, and a proximal rotation control knob fixed to the outer rim of a rotation base 30, as with the rotation control knob 18 in the fifth modification example. In this case, the sheath 5 can be rotated by operating the distal rotation control knob 18 by, for example, a thumb, or operating the proximal rotation control knob 18 by, for example, a forefinger. More specifically, when the distal rotation control knob 18 is rotated, the proximal rotation control knob 18 and the sheath 5 rotate about a longitudinal axis C together with a movable member 22. Further, when the proximal rotation control knob 18 is rotated, the distal rotation control knob 18 and the sheath 5 rotate about the longitudinal axis C together with the movable member 22.

In the foregoing embodiments and the like, the medical treatment implement (1) has the holdable housing (3) and the sheath (5), which is extended along the longitudinal axis (C) from the proximal side toward the distal side and which is rotatable about the longitudinal axis (C) with respect to the housing (3). The sheath (5) is connected to the distal side of the housing (3) such that the sheath (5) projects from the reference position (X1) of the housing (3) toward the distal side. The medical treatment implement (1) includes the end effector (7), which is attached to the distal side of the sheath (5) and which articulates with respect to the sheath (5), causing the angle of the sheath (5) with respect to the longitudinal axis (C) to change, and the drive members (41A, 41B), which are connected to the end effector (7) and which, when driven, cause the end effector (7) to articulate with respect to the sheath (5). Further, the medical treatment implement (1) includes the articulation control input units (20; 50), each of which drives the drive members (41A, 41B) in response to an operation input and rotates about the longitudinal axis (C) together with the sheath (5) with respect to the housing (3) when the sheath (5) rotates. Each of the articulation control input units (20; 50) is attached to the housing (3) at a position closer to the proximal side than the reference position (X1) of the housing (3).

The above has described the embodiments and the like. The present invention, however, is not limited to the foregoing embodiments and the like, and a variety of modifications can be obviously made without departing from the spirit of the present invention.

The invention claimed is:

1. A medical treatment implement comprising:
   an elongated shaft configured to extend along a longitudinal axis;
   a housing comprising a distal portion and a proximal portion, a proximal end of the elongated shaft being attached to the distal portion of the housing such that the longitudinal axis extends from the distal portion to the proximal portion, wherein the elongated shaft is configured to be rotatable about the longitudinal axis with respect to the housing;
   an end effector attached to a distal end of the elongated shaft, wherein the end effector is configured to articulate with respect to the longitudinal axis of the elongated shaft;
   a driver having an output end, the output end of the driver being connected to the end effector, the driver being configured to transmit a driving force to the end effector via the output end so as to articulate the end effector with respect to the elongated shaft; and
   an articulation control input member attached to the housing at a position closer to the proximal portion than the distal portion, the articulation control input member being configured to receive an operation force so as to transmit the driving force to the end effector through the driver, the articulation control input member being configured to rotate about the longitudinal axis together with the elongated shaft with respect to the housing;
   wherein the rotation of the articulation control input member about the longitudinal axis is configured to cause the end effector to rotate together with the articulation control input member and the elongated shaft with respect to the housing.

2. The medical treatment implement according to claim 1, wherein the rotation of the elongated shaft about the longitudinal axis is configured to cause a rotational force to be transmitted from the elongated shaft so that the articulation control input member rotates about the longitudinal axis together with the elongated shaft.

3. The medical treatment implement according to claim 2, further comprising a rotation control input member attached to the housing, the rotation control unit input member being configured to receive a rotational operation force so as to transmit the rotational force to the elongated shaft, thereby rotating the elongated shaft, the end effector and the articulation control input member about the longitudinal axis.

4. The medical treatment implement according to claim 3, wherein
the rotation control input member is connected to the distal portion of the housing, and
the articulation control input member is positioned apart from the rotation control input member toward a proximal side.

5. The medical treatment implement according to claim 1, further comprising a movable member connected to the elongated shaft and the articulation control input member, the movable member being rotatable about the longitudinal axis together with the elongated shaft, the end effector and the articulation control input member with respect to the housing, and the movable member being movable along the longitudinal axis with respect to the elongated shaft, the articulation control input member, and the housing.

6. The medical treatment implement according to claim 5, wherein the end effector comprises a first gripping piece and a second gripping piece which moves away from or toward the first gripping piece to open or close one or more of the first gripping piece and second gripping piece relative to the other of the first gripping piece and second gripping piece.

7. The medical treatment implement according to claim 1, wherein the housing comprises an installation outer surface configured to be directed toward a proximal side, the articulation control input member being installed on the installation outer surface.

8. The medical treatment implement according to claim 7, wherein the installation outer surface of the housing forms a proximal end outer surface of the housing.

9. The medical treatment implement according to claim 1, wherein the longitudinal axis of the elongated shaft is configured to pass the articulation control input member regardless of the angular position of the articulation control input member about the longitudinal axis.

10. The medical treatment implement according to claim 1, wherein the driver comprises a pulley rotatable with the articulation control input member and one or more articulation wires connected at one end to the pulley and at another end to the end effector.

11. The medical treatment implement according to claim 1, wherein the driver comprises a first toothed wheel movable with the articulation control input member, a second toothed wheel engaged with the first toothed wheel and movable upon movement of the first toothed wheel, and one or more articulation wires connected at one end to the second toothed wheel and at another end to the end effector.

12. The medical treatment implement according to claim 11, wherein the second toothed wheel is movable in rotations and the driver further comprises a pulley rotatable with the second toothed wheel.

13. The medical treatment implement according to claim 11, wherein the first toothed wheel is movable in rotation.

14. The medical treatment implement according to claim 1, further comprising a tubular member connecting the elongated shaft to the articulation control input member such that the elongated shaft rotates together with the articulation control input member, the tubular member further being capable of moving in translation relative to the articulation control input member.

15. The medical treatment implement according to claim 14, wherein the tubular member is configured to house at least a portion of the driver in an internal lumen.

* * * * *